(12) United States Patent
Bellani et al.

(10) Patent No.: US 9,981,098 B2
(45) Date of Patent: May 29, 2018

(54) APPARATUS FOR ASSISTED VENTILATION AND CORRESPONDING REGULATION METHOD

(71) Applicant: Dräger Medical GmbH, Lübeck (DE)

(72) Inventors: Giacomo Bellani, Carate Brianza (IT); Antonio Pesenti, Milan (IT); Antonino Nicolò Patroniti, Lissone (IT); Tommaso Mauri, Carate Brianza (IT)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 726 days.

(21) Appl. No.: 14/386,110

(22) PCT Filed: Mar. 19, 2013

(86) PCT No.: PCT/IB2013/000432
§ 371 (c)(1),
(2) Date: Sep. 18, 2014

(87) PCT Pub. No.: WO2013/140229
PCT Pub. Date: Sep. 26, 2013

(65) Prior Publication Data
US 2015/0059752 A1  Mar. 5, 2015

(30) Foreign Application Priority Data
Mar. 19, 2012  (IT) .............. MI2012A0428

(51) Int. Cl.
*A61M 16/00* (2006.01)
*A61M 16/20* (2006.01)

(52) U.S. Cl.
CPC .... *A61M 16/0069* (2014.02); *A61M 16/0003* (2014.02); *A61M 16/024* (2017.08);
(Continued)

(58) Field of Classification Search
CPC ... A61B 5/1107; A61B 5/0806; A61B 5/0816; A61M 16/00; A61M 16/0003;
(Continued)

(56) References Cited

U.S. PATENT DOCUMENTS 5,042,470 A * 8/1991 Kanesaka ......... A61M 16/0051
128/202.22
5,820,560 A * 10/1998 Sinderby ............ A61B 5/04884
600/546
(Continued)

FOREIGN PATENT DOCUMENTS

CN  101657152 A  2/2010
CN  101674859 A  3/2010
(Continued)

OTHER PUBLICATIONS

Emeriaud, Guillaume, et al. "Diaphragm electrical activity during expiration in mechanically ventilated infants." Pediatric research 59.5 (2006): 705-710. Retrieved from https://www.nature.com/articles/pr2006150.*
(Continued)

*Primary Examiner* — Tan-Uyen (Jackie) T Ho
*Assistant Examiner* — Joseph D Boecker
(74) *Attorney, Agent, or Firm* — McGlew and Tuttle, P.C.

(57) ABSTRACT

An apparatus, for assisted ventilation (1), includes at least one ventilatory device (2) connected to and controlled by a driver (3), and at least one sensor device (4) connected to the driver (3) and adapted to provide it with a signal of electrical activity produced by the diaphragm. The apparatus further includes at least one calculation device (5) connected to the driver (3), to the sensor device (4) and to the ventilatory device (2), the calculation device (5) receiving from the sensor device (4) a signal of diaphragmatic activity (Eadi) and from the ventilatory device (2) a ventilatory pressure
(Continued)

signal (Paw) and providing the driver (3) with calibration parameters (Cal) calculated on the basis of a signal of diaphragmatic electrical activity (Eadi*) and a ventilatory pressure signal (Paw*) upon switching-off said ventilatory device (2) so as to cause an expiratory pause.

19 Claims, 4 Drawing Sheets

(52) U.S. Cl.
CPC ........ *A61M 16/204* (2014.02); *A61M 16/205* (2014.02); *A61M 2016/0027* (2013.01); *A61M 2205/3327* (2013.01); *A61M 2205/3331* (2013.01); *A61M 2205/50* (2013.01); *A61M 2210/1014* (2013.01); *A61M 2230/60* (2013.01)

(58) Field of Classification Search
CPC .......... A61M 16/0057; A61M 16/0069; A61M 16/021; A61M 16/022; A61M 16/024; A61M 16/202; A61M 16/203; A61M 16/204; A61M 16/205; A61M 2016/0015; A61M 2016/0018; A61M 2016/0027; A61M 2210/1014; A61M 2230/005
See application file for complete search history.

(56) References Cited

U.S. PATENT DOCUMENTS

| | | | |
|---|---|---|---|
| 6,588,423 B1* | 7/2003 | Sinderby | A61B 5/04884 128/200.24 |
| 6,962,155 B1 | 11/2005 | Sinderby | |
| 6,974,418 B1* | 12/2005 | Hutchinson | A61B 5/02156 600/301 |
| 7,011,091 B2 | 3/2006 | Hill et al. | |
| 8,863,742 B2* | 10/2014 | Blomquist | A61B 5/04884 128/204.23 |
| 2003/0066528 A1* | 4/2003 | Hill | A61M 16/026 128/204.18 |
| 2005/0211246 A1* | 9/2005 | Beck | A61M 16/024 128/204.23 |
| 2009/0159082 A1† | 6/2009 | Eger | |
| 2010/0180896 A1 | 7/2010 | Blomquist | |
| 2010/0252038 A1* | 10/2010 | Lagerborg | A61B 5/0488 128/204.23 |
| 2011/0301482 A1* | 12/2011 | Sinderby | A61B 5/0488 600/529 |
| 2012/0006327 A1* | 1/2012 | Sinderby | A61M 16/0051 128/204.23 |
| 2012/0103334 A1* | 5/2012 | Sinderby | A61B 5/08 128/204.18 |
| 2012/0152250 A1* | 6/2012 | Eger | A61B 5/0488 128/204.23 |
| 2014/0296728 A1* | 10/2014 | Sinderby | A61B 5/08 600/529 |
| 2016/0121064 A1* | 5/2016 | Rees | A61M 16/026 128/204.23 |
| 2017/0128684 A1* | 5/2017 | Sinderby | A61M 16/024 |

FOREIGN PATENT DOCUMENTS

| | | | |
|---|---|---|---|
| WO | 2010081230 | † | 7/2010 |
| WO | 2010081230 A1 | | 7/2010 |

OTHER PUBLICATIONS

P. Navalesi, D. Colombo, F. Della Corte, NAVA Ventilation, Minerva Anestesiologica, pp. 346-352, May 2010.
Chinese Search Report dated Aug. 25, 2015.
Italian Search Report dated Nov. 16, 2012.
P. Navalesi, D. Colombo, F. Della Corte; "NAVA Ventilation", Minerva Anestesiologica, pp. 346-352 published in May 2010.†

* cited by examiner
† cited by third party $$PEI = \frac{Paw^*}{Eadi^*}$$

APPARATUS FOR ASSISTED VENTILATION AND CORRESPONDING REGULATION METHOD

CROSS REFERENCE TO RELATED APPLICATIONS

This application is a United States National Phase Application of International Application PCT/IB2013/000432 filed Mar. 19, 2013 and claims the benefit of priority under 35 U.S.C. § 119 of Italian Patent Application MI2012A000428 filed Mar. 19, 2012, the entire contents of which are incorporated herein by reference.

FIELD OF THE INVENTION

The present invention refers to an apparatus for assisted ventilation. The invention also refers to a method for regulation of an assisted ventilation.

BACKGROUND OF THE INVENTION

As is well-known, artificial ventilation (artificial respiration), also known as assisted or mechanical ventilation (assisted or mechanical respiration), replaces or supplements the activity of the inspiratory muscles of a subject, supplying the energy needed to ensure an adequate volume of gas for the lungs.

Usually a distinction is made between permanent assisted ventilation and temporary assisted ventilation.

Permanent assisted ventilation is usually performed by means of a negative ventilation system, using an air chamber which surrounds the chest, such as a "iron lung", and which is rhythmically brought to a negative pressure so as to allow the aspiration of air into the airways and the lungs.

Temporary artificial ventilation is based instead on the use of positive pressure systems such as a ventilator or a simple oxygen-enriched air chamber, such as the Ambu bag or bag valve mask, which are connected to the airways and rhythmically operated, for example by means of a manual compression, so as to force air into these airways and therefore into the lungs.

In order to ensure an easy passage of the air inside the airways and isolation of the latter, the direct connection to the positive pressure source is performed by inserting a cannula into the larynx via the nose or the mouth, or by means of a tracheotomy. In other cases it is possible to perform simple actions on the airways or the laryngeal mask which is a substitute for the endotracheal tube.

Artificial ventilation is for example used in surgical operations which envisage curarization of the subject with consequent muscular paralysis and when the spontaneous respiration of the subject is no longer able to maintain the vital functions.

Among the many conditions which require artificial ventilation it is possible to mention also the presence of acute pulmonary lesion or apnea due to a respiratory arrest, including intoxication, but also the presence of a paralysis of the diaphragm as in acute crises tied to muscular dystrophy or amyotrophic lateral sclerosis or in the case of a spinal cord injury.

Assisted ventilation is also used in the case of reacutized chronic pulmonary diseases, acute respiratory acidosis or hypoxia, hypotension and shock, as in congestive heart failure or during sepsis.

All the methods of assisted ventilation share the general concept that part of the work is performed by the subject undergoing assisted ventilation, by means of generation of a negative muscle pressure (Pmusc) via the subject's inspiratory muscles, mainly the diaphragm, so as to recall air inside the lungs, and part of the work is instead performed by the assisted ventilation apparatus.

In particular, during the assisted ventilation, the subject is connected to a mechanical respirator or ventilator, via a tube positioned in the trachea, the flow of gas towards the subject (inhalation or inspiration) and from the subject (exhalation or expiration) being regulated by the ventilator itself.

In greater detail, the modern assisted-ventilation apparatuses envisage that, when the apparatus registers that the subject has started to breathe, the ventilator assists him/her, causing an increase in the pressure in the airways and consequently an increase in the flow of gas directed towards the subject (inspiration). In this way, the pressure needed to displace the gas is provided partly by the ventilator and partly by the subject, in a manner proportional to his/her muscle pressure (Pmusc).

In practice, it is therefore important to be able to estimate the spontaneous respiratory activity or the muscle pressure (Pmusc) being autonomously generated by the subject, since an underestimated assisted ventilation may cause tiredness and, more generally, problems for the subject undergoing the assisted ventilation, but also an excessive assisted ventilation may in any case cause, in addition to an increase in the oxygen consumption, problems for the subject. In particular, it is important to avoid the occurrence of ventilatory asynchrony between the subject and the assisted ventilation apparatus or ventilator, which has proved to be extremely damaging, in particular for subjects undergoing the assisted ventilation for a prolonged period of time.

At present, the reference standard for measurement of the muscle pressure (Pmusc) provided by a subject, and therefore an evaluation of the spontaneous breathing activity, is the measurement of the oesophageal pressure which requires in particular positioning of a balloon inside the oesophagus of the subject, connected to a transducer for detecting the oesophageal pressure, and on the basis of which the pressure inside the thorax and therefore the muscle pressure (Pmusc) provided by the subject is estimated.

This method, however, is rarely used in practice, not so much because it is invasive, but because it is technically complex with regard to interpretation of the data.

Other surrogate indices for evaluation of the spontaneous breathing activity, namely the respiratory work performed autonomously by a subject, have been developed; these include the so-called P0.1 (namely the pressure generated by the subject in the first 100 milliseconds from the start of inspiration during an expiratory occlusion) which is the most widely used index.

The most recent assisted-ventilation technologies, such as the NAVA® ("Neurally Adjusted Ventilatory Assist") technology, instead have an approach to the assisted ventilation which is based on the neural respiratory emission, with detection of the electrical activity of the diaphragm.

It is in fact known that the respiratory action is controlled by the respiratory center of the brain, which establishes the characteristics of each breath, the duration and the amplitude. The respiratory center sends a signal along the phrenic nerve and activates the muscle cells of the diaphragm, causing contraction thereof and the descent of the diaphragmatic dome. Consequently, the pressure in the airways drops, causing a flow of air into the lungs.

The assisted ventilation apparatuses based on the NAVA® technology therefore receive a signal of the electrical activity produced by the diaphragm (Eadi) and use this signal to assist the respiration of the subject in synchronism, the work of the ventilator and that of the diaphragm being controlled by the same signal, such as to ensure simultaneous and synchronized cooperation between the diaphragm and ventilator. In this way the assisted ventilation is provided independently of conventional pneumatic sensors, such as the oesophageal balloon, and is not influenced by the air losses associated with the interfaces of the subjects, this being a very important condition for example in the case of a treatment of children who generally have a muscle pressure (Pmusc) which is too weak to be detected precisely by pressure or flow mechanisms.

Synchronization of the assisted ventilation with the respiratory activity associated with the spontaneous breathing activity of the subject in particular eliminates the lack of uniformity with the duration of the air inspiration and expiration by the subject, avoiding the risk of an inefficient effort and allowing lower assistance levels to be used.

Furthermore, the signal of the electrical activity as produced by the diaphragm (Eadi) is used to evaluate the conditions of the subject and in particular to decide when to perform the extubation of the subject, in particular when the amplitude of the electrical activity signal Eadi as produced by the diaphragm falls below a certain limit.

SUMMARY OF THE INVENTION

The technical problem of the present invention is that of further improving the performance of an apparatus for assisted ventilation by means of a method for regulation thereof, using the signal of the electrical activity as produced by the diaphragm and having structural and functional characteristics such as to overcome the limitations and drawbacks which hitherto limit the apparatuses designed in accordance with the prior art and in particular avoid the need to detect an oesophageal pressure signal.

The idea of solution at the basis of the present invention is that of performing an interruption of the assisted ventilation provided by an assisted ventilation apparatus, during which it is possible to estimate the muscle pressure produced by a subject on the basis of the value of the signal of the diaphragmatic electrical activity and a value of the ventilatory pressure as detected during said interruption, so as to regulate the assisted ventilation provided by the said apparatus in a "tailor-made" manner.

On the basis of this idea of solution the technical problem is solved by an apparatus for assisted ventilation comprising at least one ventilatory device connected to and controlled by a driver (drive device), as well as a sensor (sensor device) connected to the driver and adapted to provide it with a signal of electrical activity produced by the diaphragm, the apparatus being characterized in that it further comprises at least one calculation device, connected to the driver, to the sensor device and to the ventilatory device, this calculation device receiving from the sensor device a signal of diaphragmatic electrical activity and from the ventilatory device a ventilatory pressure signal, and providing the driver with calibration parameters calculated on the basis of a signal of diaphragmatic activity and a ventilatory pressure signal upon switching-off the ventilatory device so as to cause an expiratory pause.

More particularly, the invention comprises the following additional and optional features which may be taken alone or in combination one another.

According to an aspect of the invention, the apparatus may comprise a switch device connected to the driver and providing it with a pause signal which forces the driver to temporarily switch off the ventilatory device so as to cause the expiratory pause.

According to another aspect of the invention, the apparatus may further comprise at least one synchronization device connected to the calculation device and the switch device and providing them with a synchronization signal.

In particular, the synchronization signal may be manually generated or have a frequency established a priori.

According to an aspect of the invention, the calculation device may comprise a display for displaying the calibration parameters.

Furthermore, the ventilatory device may provide a ventilatory pressure signal during the expiratory pause which corresponds to a value of the spontaneous breathing activity and therefore of the muscle pressure produced by the subject and the calculation device may provide calibration parameters for regulating the assisted ventilation provided by the ventilatory device on the basis of this value of the muscle pressure produced by the subject as calculated.

The problem is also solved by a method for regulation of an assisted ventilation comprising the steps of:
providing an apparatus for assisted ventilation comprising at least one ventilatory device controlled by a driver, at least one sensor device adapted to provide the driver with a signal of electrical activity produced by the diaphragm of a subject, and a calculation device, suitably connected to the driver as well as to the sensor device and to the ventilator device;
providing the driver with a signal of diaphragmatic electrical activity via the sensor device;
subsequently providing the calculation device with a ventilatory pressure signal emitted by the ventilatory device and a further signal of diaphragmatic electrical activity obtained via the sensor device during an expiratory pause caused by switching-off the ventilatory device;
calculating, on the basis of the ventilatory pressure signal and of the further signal of diaphragmatic electrical activity during the expiratory pause, a value of the spontaneous breathing activity and therefore of the muscle pressure produced by the subject; and providing calibration parameters for regulating the assisted ventilation provided by the ventilatory device on the basis of the value of the muscle pressure produced by the subject as calculated.

According to an aspect of the invention, the method may comprise further a step of synchronizing the steps of providing the ventilatory pressure signal and the signal of diaphragmatic electrical activity and calculating the value of the spontaneous breathing activity by means of a synchronization signal supplied to the calculation device and to the switch device that causes switching-off the ventilatory unit.

Furthermore, the method may comprise different steps for calculating the value of the spontaneous breathing activity and regulating the assisted ventilation according to a value of assisted ventilation provided by the ventilatory device on the basis of the value of the spontaneous breathing activity as calculated during a plurality of expiratory pauses.

According to another aspect of the invention, the method may further comprise a step of calculating a parameter for assessing the spontaneous breathing activity of the subject as a ratio between the ventilatory pressure signal and the further signal of diaphragmatic electrical activity during the expiratory pause.

Finally, the method may further comprise a step of estimating for each instant a value of the spontaneous breathing activity of the subject by multiplying the parameter for assessing the spontaneous breathing activity and the signal of diaphragmatic electrical activity.

The characteristic features and advantages of the apparatus for assisted ventilation and of the regulation method according to the invention will emerge from the description provided herein below of an embodiment thereof, given by way of a non-limiting example, with reference to the accompanying drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
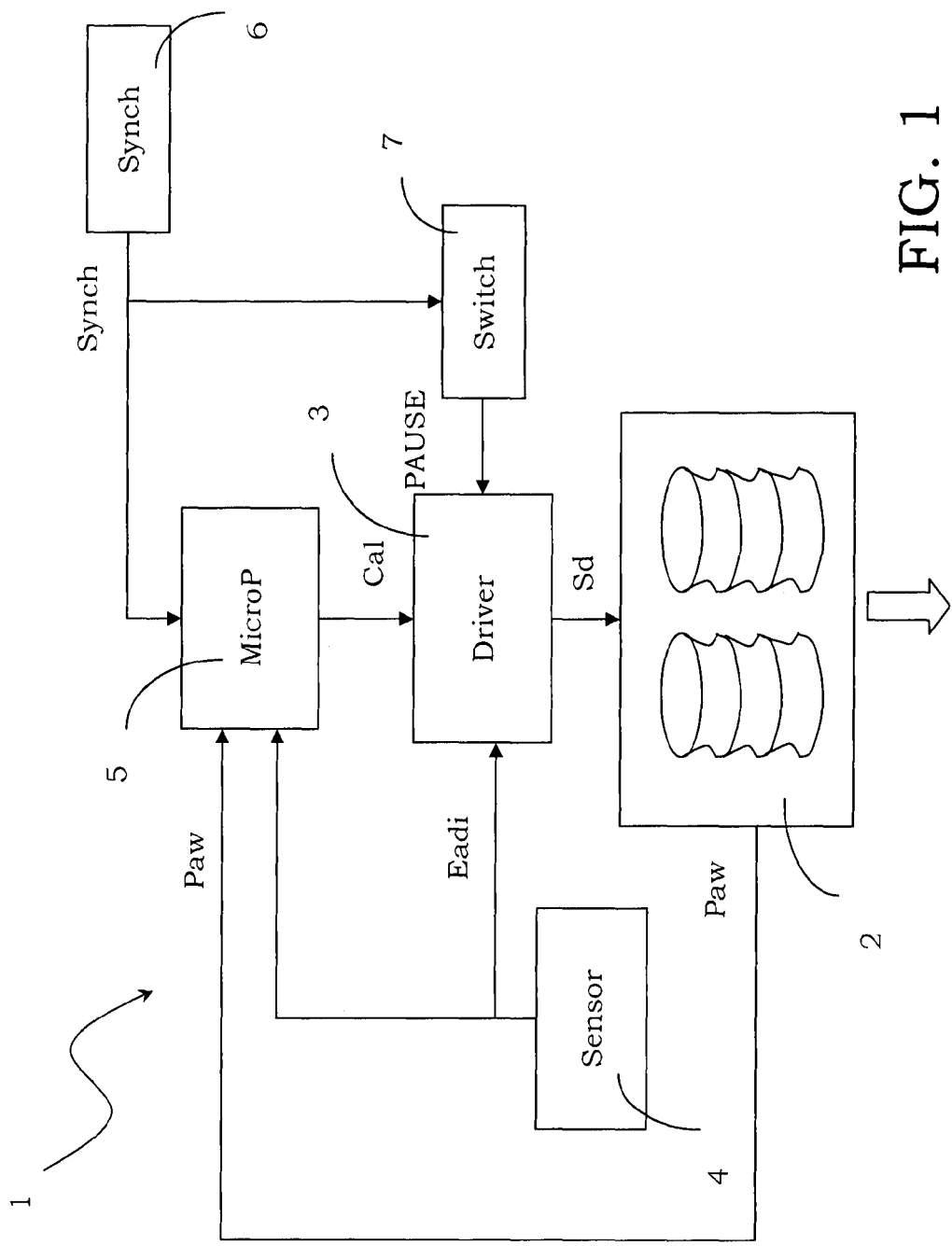
FIG. 1 is a schematic view showing an apparatus for assisted ventilation which implements the regulation method according to the invention.

Referring to the Figures, and in particular to FIG. 1, an apparatus for assisted ventilation realized in accordance with the invention is indicated with 1 as a whole. As will become clear from the continuation of the description, the apparatus 1 for assisted ventilation is able to implement the method for regulation of an assisted ventilation according to the invention.

The present invention is based on the consideration that the electrical activity produced by the diaphragm (Eadi) is proportional to the muscle pressure (Pmusc) which determines the respiratory activity of a subject, in accordance with a proportionality coefficient which, however, is variable from one subject to another and cannot be predicted in advance, in order to evaluate the given contribution to breathing as a result of this muscle pressure (Pmusc), namely the spontaneous breathing activity of the subject.

Moreover, it may be assumed that this proportionality coefficient may differ not only between different subjects, for example subjects with different lengths of the diaphragmatic fibres, but also in the case of the same subject, for example in case of different respiratory muscle conditions.

This variability of the proportionality coefficient between electrical activity produced by the diaphragm (Eadi) and muscle pressure (Pmusc) which determines the spontaneous breathing activity of a subject makes it difficult to perform a correct initial setting of the apparatus for assisted ventilation, based essentially on statistical and empirical conditions, and also prevents a correct calibration during working. In particular, setting of the assisted ventilation is at present performed empirically, setting the corresponding ventilator to a number of reference values and evaluating the response of a subject undergoing the assisted ventilation.

The regulation method according to the invention provides a solution to these problems, as will be clarified below, by obtaining and using the spontaneous breathing activity of a subject undergoing the assisted ventilation as a basis for evaluating which percentage of the total pressure provided by the respiratory system may be regarded as being attributable to the subject, and thus being able to regulate the assisted ventilation by defining a specific percentage of the pressure provided by the ventilator in relation to the muscle pressure produced by the subject.

The regulation method according to the invention is in particular implemented by means of the apparatus 1 for assisted ventilation of FIG. 1.

Such an apparatus 1 for assisted ventilation essentially comprises an actual ventilatory device 2 controlled by a suitable driver 3 connected thereto. Furthermore, the apparatus 1 for assisted ventilation comprises at least one sensor device 4 connected to the driver 3 and adapted to provide it with a signal Eadi of diaphragmatic electrical activity.

According to an aspect of the invention, the apparatus 1 for assisted ventilation further comprises a calculation device 5 suitably connected to the driver 3 and also to the sensor device 4 and to the actual ventilatory device 2.

In particular, the calculation device 5 receives from the sensor device 4 the signal Eadi of diaphragmatic electrical activity and from the ventilatory device 2 a ventilatory pressure signal Paw, namely the pressure signal of the airways, and provides the driver 3 with calibration parameters Cal. In particular, the calibration parameters Cal are calculated on the basis of a signal Eadi* of diaphragmatic electrical activity and a signal Paw* of ventilatory pressure, namely the muscle pressure (Pmusc) produced by the subject, upon switching-off the ventilatory device so as to cause an expiratory pause.

Alternatively, the calculation device 5 is provided with a display for displaying the calibration parameters which may be introduced into the driver 3 by an operator.

Furthermore, the apparatus 1 for assisted ventilation comprises a synchronization device 6 adapted to supply a synchronization signal Synch to the calculation device 5 and the switch device 7, which is in turn connected to the driver 3 and adapted to provide the latter with a pause signal PAUSE which forces the driver 3 to temporarily switch off the ventilatory device 2 so as to cause an expiratory pause, in particular closing the inspiratory and expiratory valves of the ventilatory device 2 itself. The synchronization signal Synch may be manually generated or have a frequency established a priori.

Essentially, switching-off the ventilatory device 2, in particular closing its inspiratory and expiratory valves, produces an expiratory pause where the ventilatory pressure signal Paw is determined solely by the muscle pressure (Pmusc) produced by the subject, namely by his/her spontaneous breathing activity.

Obviously, at the end of the pause signal PAUSE, the ventilatory device 2 resumes the assisted ventilation.

In this way, the apparatus 1 for assisted ventilation is able to implement the method according to the invention.

The present invention also refers to a method for regulation of an assisted ventilation comprising the steps of:
- providing an apparatus 1 for assisted ventilation comprising a ventilatory device 2 controlled by a driver 3, at least one sensor device 3 adapted to provide the driver 3 with a signal of electrical activity produced by the diaphragm of a subject, and a calculation device 5, suitably connected to the driver 3 and also to the sensor device 4 and to the ventilatory device 2;
- providing the driver 3 with a signal Eadi of diaphragmatic electrical activity via said sensor device 4;
- subsequently providing the calculation device 5 with a ventilatory pressure signal Paw* emitted by the ventilatory device 2 and a further signal Eadi* of diaphragmatic electrical activity obtained via the sensor device during an expiratory pause caused by switching-off said ventilatory device 2;
- calculating, on the basis of the ventilatory pressure signal Paw* and of the further signal Eadi* of diaphragmatic electrical activity during said expiratory pause, a value of the spontaneous breathing activity and therefore of the muscle pressure (Pmusc) produced by the subject; and
- providing calibration parameters Cal for regulating said assisted ventilation provided by the ventilatory device on the basis of the value of the muscle pressure (Pmusc) produced by the subject as calculated.

Advantageously, according to the invention, the method comprises a step of synchronizing the steps of providing the ventilatory pressure signal Paw and the signal Eadi of diaphragmatic electrical activity and calculating the value of the assisted ventilation provided by the ventilatory device 2 by means of a synchronization signal Synch supplied to said calculation device 5 and to said switch device 7 in order to obtain switching-off the ventilatory device 2.

Obviously, once the assisted ventilation has been regulated on the basis of the muscle pressure (Pmusc) produced by the subject as calculated depending on the ventilatory pressure signal Paw* emitted by the ventilatory device and the further signal Eadi* of diaphragmatic ventilatory activity during the expiratory pause, the assisted ventilation is subsequently resumed by switching-on again, after interruption of the pause signal PAUSE, the ventilatory device 2 regulated by means of the calibration parameters Cal.

It is possible to envisage a plurality of expiratory pauses during which successive operations for regulating the assisted ventilation may be performed. These expiratory pauses may be manually controlled or may have a frequency established a priori.

The method also comprises a step of calculating a parameter PEI for assessing the spontaneous breathing activity of a subject. In particular, the parameter PEI is calculated as a ratio between the ventilatory pressure signal Paw* and the further signal Eadi* of diaphragmatic electrical activity during an expiratory pause. This parameter PEI may be then used to estimate at any moment the spontaneous breathing activity of the subject in terms of spontaneous ventilatory pressure, by simply multiplying this parameter PEI by the value of the signal Eadi of diaphragmatic activity obtained from the subject.

According to another aspect, the invention further describes a parameter PEI for assessing the spontaneous breathing activity of a subject being calculated as a ratio between a value of the ventilatory pressure signal Paw* and the further signal Eadi* of diaphragmatic electrical activity during an expiratory pause of an apparatus 1 for assisted ventilation.

$$PEI = Paw^* / Eadi^*$$

where Paw* and Eadi* are the values of the ventilatory pressure signal Paw and the signal Eadi of diaphragmatic electrical activity during the expiratory pause, the value Paw* therefore corresponding to the muscle pressure (Pmusc) which determines the spontaneous breathing activity of the subject during this pause.

According to a further aspect, the invention relates to a method for monitoring the breathing activity of a subject undergoing the assisted ventilation comprising the steps of:
- providing a signal Eadi* of diaphragmatic electrical activity and a signal Paw* of ventilatory pressure during an expiratory pause of the subject;
- calculating a parameter PEI for assessing the spontaneous breathing activity of the subject as a ratio between the values of the ventilatory pressure signal Paw* and the signal Eadi* of diaphragmatic electrical activity during the expiratory pause; and
- monitoring the respiratory activity of the subject estimated for each instant by multiplying this parameter PEI by instantaneous values of a signal Eadi* of diaphragmatic electrical activity of the subject.

The monitoring method also provides for displaying the pattern of the respiratory activity of the subject as estimated, for example by means of a display.

Figure 2A:
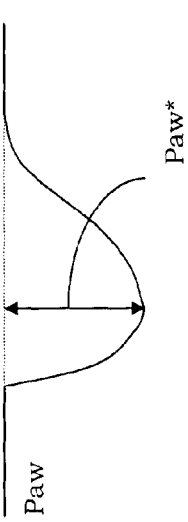
FIG. 2A is a schematic illustration of the pattern of signals of the apparatus according to FIG. 1 in a first working condition.
Figure 2B:
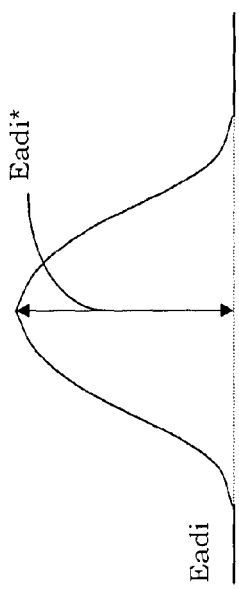
FIG. 2B is a schematic illustration of the pattern of signals of the apparatus according to FIG. 1 in a first working condition.

FIGS. 2A and 2B show the patterns of the ventilatory pressure signal Paw* and the signal Eadi* of electrical diaphragmatic activity during an expiratory pause.

In the example shown in these figures, the value of the ventilatory pressure signal Paw* is equal to 3 $cmH_2O$, while the value of the signal Eadi* of diaphragmatic electrical activity is equal to 6 microV, purely by way of a guide, resulting in a parameter PEI equal to 0.5 $cmH_2O$/microV.

Figure 3A:
FIG. 3A is a schematic illustration of the pattern of signals of the apparatus according to FIG. 1 in a second working condition.
Figure 3B:
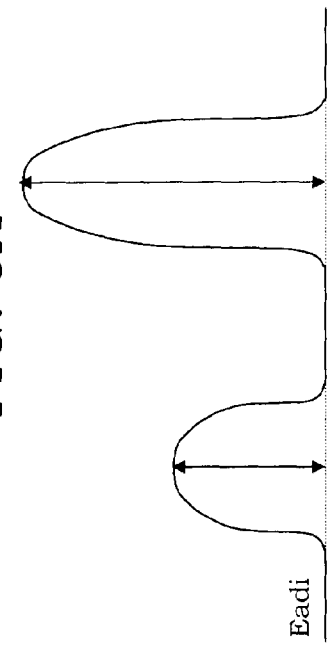
FIG. 3B is a schematic illustration of the pattern of signals of the apparatus according to FIG. 1 in a second working condition.
Figure 3C:
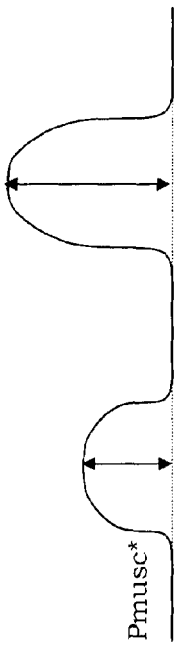
FIG. 3C is a schematic illustration of the pattern of signals of the apparatus according to FIG. 1 in a second working condition.

It should be noted that the parameter PEI essentially specifies how many units, expressed for example in centimeters of water $cmH_2O$, of a muscle pressure (Pmusc) associated with the spontaneous breathing activity of the subject are generated as a result of 1 microV of an electrical activity produced by the diaphragm for a specific subject and in specific conditions, then evaluating the corresponding spontaneous breathing activity. It is then possible, after obtaining the parameter PEI, to calculate at any instant the value of the muscle pressure (Pmusc) being associated with the spontaneous breathing activity of the subject by simply multiplying this parameter PEI by the value of the signal Eadi of diaphragmatic electrical activity, without having any longer to measure the oesophageal pressure, as shown in FIGS. 3A-3C which illustrate, respectively, a ventilatory pressure signal Paw obtained with a conventional apparatus for assisted ventilation, the signal Eadi of diaphragmatic electrical activity and a signal Pmusc* of muscle pressure produced by the subject, as calculated by means of the method according to the invention, i.e. by multiplying for each instant the value of the signal Eadi of diaphragmatic electrical activity by the parameter PEI calculated during a preceding expiratory pause, in the example equal to 0.5 $cmH_2O$/microV. As seen, owing to the value of the signal Pmusc* of muscle pressure produced by the subject, as calculated by means of the method according to the invention, it is therefore possible to set in an optimum manner the assisted ventilation provided by the apparatus 1 for assisted ventilation.

Experiments have been carried out by the Applicants on subjects with acute respiratory insufficiency recovered in intensive therapy. The experiments involved ten subjects, half of them male and the other half female, with ages ranging between 43 and 83.

The subjects were each fitted with an oesophageal balloon and a nasogastric probe with a sensor for the ventilatory pressure signal Paw and a sensor for the signal Eadi of diaphragmatic electrical activity, connected to an apparatus for assisted ventilation of the NAVA® type.

Suitable pressure transducers were connected to the opening of the airways and to the oesophageal balloon and their signal was acquired, on two channels, by a data acquisition system receiving also the signals from the sensors of the nasogastric probe. The acquisition system recorded, with a sampling frequency of 100 Hz, all the waveforms mentioned above.

The used test protocol envisaged an initial check of the correct positioning of the nasogastric probe based on a standard procedure using the signal Eadi of diaphragmatic electrical activity as well as a calibration step using the oesophageal pressure.

The test protocol also consisted of three separate phases:
phase 1: the subjects were subjected to ventilation using a mechanical ventilation support system (PS ventilation), with three levels of assistance (4, 10 and 16 cmH$_2$O), having a duration of 30 minutes each, in random order. This phase presupposed that at least some subjects were subjected to overassistance at 16 cmH$_2$O: for these subjects, the level 16 cmH$_2$O was replaced with a level 0 cmH$_2$O; moreover, it was assumed that at least some of the subjects were subjected to underassistance at 4 cmH$_2$O: for these subjects, the level 4 cmH$_2$O was replaced with a level 20 cmH$_2$O.
phase 2: the subjects were then subjected to an assisted ventilation by means of a NAVA® apparatus (NV ventilation), using again three different levels of assistance, in random order, and in particular 0.5, 1 and 1.5 mV/cmH$_2$O for a duration of 30 minutes each.

During both PS ventilation and NV ventilation, a number of brief expiratory pauses (with a duration of 2-3 seconds) were performed at 10 minute intervals and, during these pauses, the ventilatory pressure signal Paw* corresponding to the value of spontaneous breathing activity of the subject was recorded.
phase 3: the subjects were sedated and subjected to mechanically controlled ventilation (MC ventilation) with a stream volume of 6-8 ml/kg, in order to measure the split compliance of the respiratory system with inspiratory and expiratory pauses.

Figure 4A:
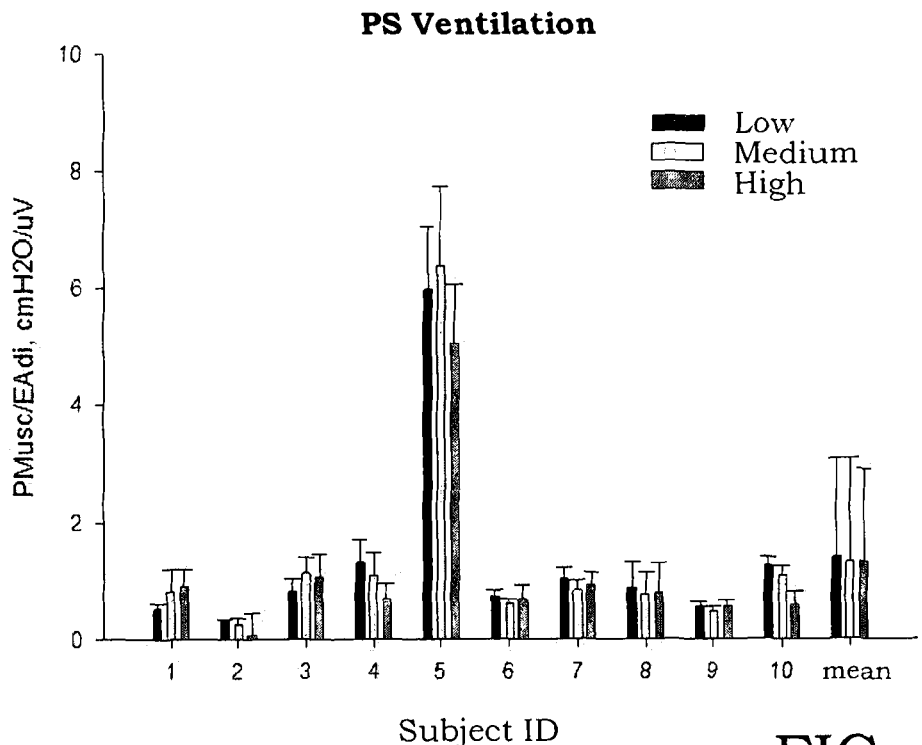
FIG. 4A is a schematic illustration of the results of experimental tests carried out by the Applicants.
Figure 4B:
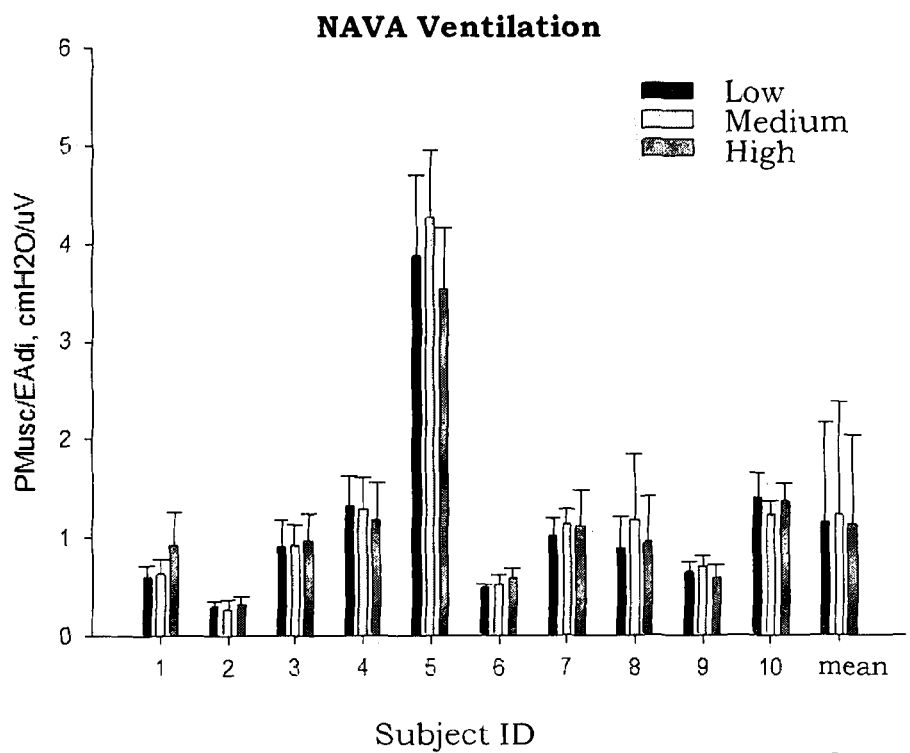
FIG. 4B is a schematic illustration of the results of experimental tests carried out by the Applicants.
Figure 5:
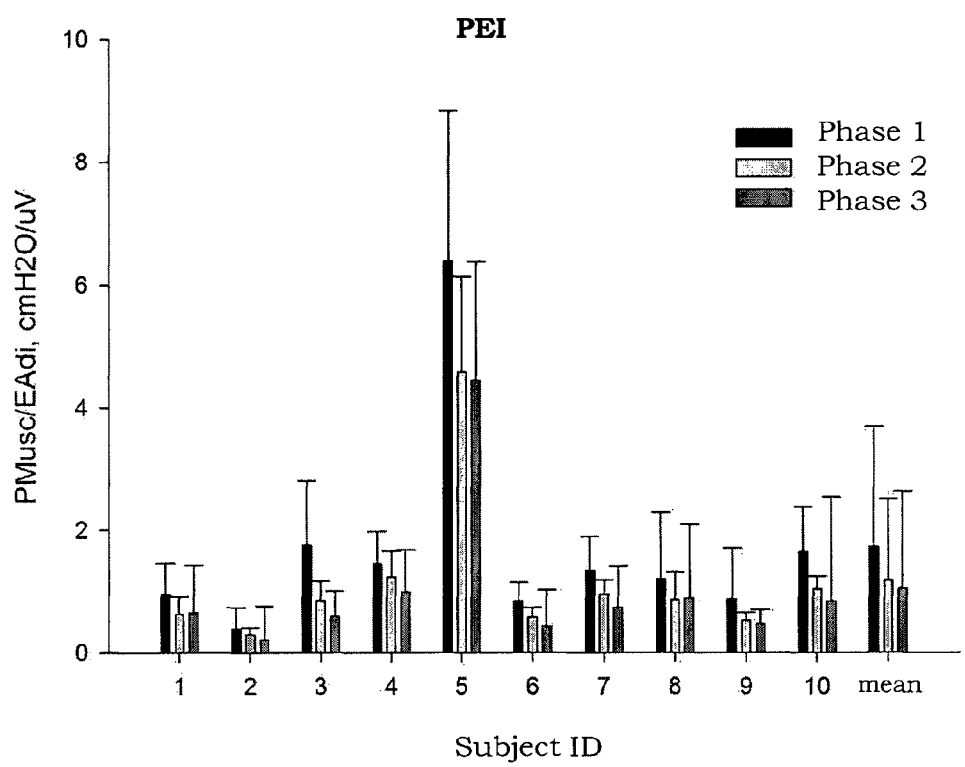
FIG. 5 is a schematic illustration of the results of experimental tests carried out by the Applicants.

The parameter PEI for assessing the spontaneous breathing activity of a subject for PS and NAVA® assisted ventilations as described above was then calculated, obtaining the results shown in FIGS. 4A and 4B, respectively, for the three levels of assistance used (and indicated in the figures as low, medium and high, respectively), as well as the value of the parameter PEI during the various phases of the respiratory cycle, as shown in FIG. 5, all of which in relation to ten subjects identified by means of numerical identification ID.

It was thus possible to verify that the value of the parameter PEI is highly variable among the various subjects, while it remains relatively stable for the same subject with different levels of assistance and types of ventilation.

On the basis of the experimental tests carried out, albeit for a limited amount of time and for a limited number of subjects involved, it is possible to conclude that the parameter PEI for assessment of the spontaneous breathing activity, obtained as in the method according to the invention during an expiratory pause, constitutes an optimum substitute for the ratio between muscle pressure (Pmusc) which determines the breathing activity of a subject and the signal Eadi of diaphragmatic activity during normal ventilation.

To conclude, the experimental tests carried out by the Applicants have shown that, in subjects with acute respiratory insufficiency, subjected to an assisted ventilation, the value of the muscle pressure (Pmusc) which determines the spontaneous breathing activity of a subject is strictly associated with the signal Eadi of diaphragmatic electrical activity, according to a proportionality index, the parameter PEI, which varies greatly between different subjects, but is fairly constant for the same subject and that the calculation of this parameter PEI from a signal Eadi* of diaphragmatic activity and from a ventilatory pressure signal Paw* during an expiratory pause is able to provide a correct estimation of the spontaneous breathing activity of a subject.

In essence, with the regulation method and the apparatus for assisted ventilation according to the invention it is possible to obtain an optimized assisted ventilation which is not only synchronized with a diaphragmatic electrical activity, but also has a value determined on the basis of the spontaneous breathing activity or of the muscle pressure (Pmusc) of the subject undergoing the assisted ventilation.

Obviously, a person skilled in the art, in order to satisfy any specific requirement which arises, may make numerous modifications and variations to the apparatus and the method described above, all of which being however contained within the scope of protection of the invention, as defined by the following claims.

While specific embodiments of the invention have been shown and described in detail to illustrate the application of the principles of the invention, it will be understood that the invention may be embodied otherwise without departing from such principles.

The invention claimed is:
1. An apparatus for assisted ventilation of a subject, the apparatus comprising:
a driver;
at least one ventilatory device connected to and controlled by the driver;
a sensor connected to said driver and adapted to provide the driver with a signal of electrical activity produced by the diaphragm of the subject; and
at least one calculation device connected to said driver, connected to said sensor and connected to said ventilatory device, said calculation device receiving from said sensor a signal of diaphragmatic electrical activity and from said ventilatory device a ventilatory pressure signal, and providing said driver with calibration parameters calculated on a basis of a signal of diaphragmatic electrical activity and a ventilatory pressure signal upon switching-off said ventilatory device so as to cause an expiratory pause.

2. An apparatus for assisted ventilation according to claim 1, further comprising a switch device connected to said driver and providing said driver with a pause signal which forces said driver to temporarily switch off said ventilatory device so as to cause said expiratory pause.

3. An apparatus for assisted ventilation according to claim 2, further comprising at least one synchronization device connected to said calculation device and connected to said switch device and providing said calculation device and said switch device with a synchronization signal.

4. An apparatus for assisted ventilation according to claim 3, wherein said synchronization signal is manually generated or has a frequency established a priori.

5. An apparatus for assisted ventilation according to claim 1, wherein said calculation device comprises a display for displaying said calibration parameters.

6. An apparatus for assisted ventilation according to claim 1, wherein:
said ventilatory device provides said ventilatory pressure signal during said expiratory pause, which ventilatory pressure signal corresponds to a value of a spontaneous breathing activity and therefore of a muscle pressure produced by said subject; and
said calculation device provides said calibration parameters for regulating said assisted ventilation provided by said ventilatory device on a basis of said value of the muscle pressure produced by said subject.

7. An apparatus for assisted ventilation according to claim 1, wherein:
said switching-off of said ventilatory device includes closing inspiratory and expiratory valves of said ventilatory device to cause said expiratory pause.

8. An apparatus for assisted ventilation according to claim 1, wherein:
said switching-off of said ventilatory device includes blocking a flow of breathing gas into and out of the subject to produce said expiratory pause.

9. A method for regulation of an assisted ventilation comprising the steps of:
providing an apparatus for assisted ventilation comprising at least one ventilatory device controlled by a driver, at least one sensor adapted to provide said driver with a signal of electrical activity produced by the diaphragm of a subject, and a calculation device suitably connected to said driver and also connected to said sensor and connected to said ventilatory device;
providing said driver with a signal of diaphragmatic electrical activity via said sensor;
subsequently providing said calculation device with a ventilatory pressure signal emitted by said ventilatory device and a further signal of diaphragmatic electrical activity (Eadi*) obtained via said sensor during an expiratory pause caused by switching-off said ventilatory device;
calculating, on a basis of said ventilatory pressure signal and of said further signal of diaphragmatic electrical activity during said expiratory pause, a value of a spontaneous breathing activity and therefore of a muscle pressure produced by said subject; and
providing calibration parameters for regulating said assisted ventilation provided by said ventilatory device on a basis of said value of the muscle pressure produced by said subject as calculated.

10. A method according to claim 9, further comprising a step of synchronizing said steps of providing said ventilatory pressure signal and said signal of diaphragmatic electrical activity and calculating said value of the spontaneous breathing activity by means of a synchronization signal supplied to said calculation device and to said switch device that causes switching-off said ventilatory device.

11. A method according to claim 10, wherein the method further comprises providing different steps for calculating said value of the spontaneous breathing activity and regulating said assisted ventilation according to a value of assisted ventilation provided by said ventilatory device on a basis of said value of the spontaneous breathing activity as calculated during a plurality of expiratory pauses.

12. A method according to claim 9, wherein the method further comprises a step of calculating a parameter for assessing the spontaneous breathing activity of said subject as a ratio between said ventilatory pressure signal and said further signal of diaphragmatic electrical activity during said expiratory pause.

13. A method according to claim 12, wherein the method further comprises a step of estimating for each instant a value of the spontaneous breathing activity of said subject by multiplying said parameter for assessing the spontaneous breathing activity and said signal of diaphragmatic electrical activity.

14. A method according to claim 9, wherein:
said switching-off of said ventilatory device includes closing inspiratory and expiratory valves of said ventilatory device to cause said expiratory pause.

15. A method according to claim 9, wherein:
said switching-off of said ventilatory device includes blocking a flow of breathing gas into and out of the subject to produce said expiratory pause.

16. A method for ventilating a subject, the method comprising the steps of:
providing a ventilator;
operating the ventilator to assist flowing breathing gas into and out of the subject;
measuring a diaphragm electrical signal during said flowing of the breathing gas;
measuring a ventilatory pressure of the breathing gas during said flowing;
blocking the flow of the breathing gas into and out of the subject to produce an expiratory pause;
recording a pause value of the diaphragm electrical signal and a pause value of the ventilatory pressure during the expiratory pause;
determining a muscle pressure of the subject representing a respiratory activity of the subject from a ratio of the pause values of the diaphragm electrical signal and the ventilatory pressure;
said operating of the ventilator being performed to assist said flowing of breathing gas as a function of the muscle pressure.

17. A method in accordance with claim 16, wherein:
said operating of the ventilator is performed to regulate assisted ventilation of the subject by defining a specific percentage of the pressure provided by the ventilator in relation to the muscle pressure produced by the subject.

18. A method in accordance with claim 16, wherein:
a total pressure of the breathing gas includes breathing gas pressure from the ventilator and breathing gas pressure from the subject;
determining of the breathing gas pressure from the subject is performed using the determined muscle pressure.

19. A method in accordance with claim 18, wherein:
said operating of the ventilator is performed to regulate assisted ventilation of the subject by defining a specific percentage of the pressure provided by the ventilator in relation to the muscle pressure produced by the subject.

* * * * *